US011247038B2

(12) United States Patent
Hoss et al.

(10) Patent No.: US 11,247,038 B2
(45) Date of Patent: Feb. 15, 2022

(54) MATRIX-CODED MEDICAL DEVICE TRACKER AND MAINTENANCE

(71) Applicant: Physio-Control, Inc., Redmond, WA (US)

(72) Inventors: Jennifer Elaine Hoss, Seattle, WA (US); Kevin C. Drew, Snohomish, WA (US); Mitchell A. Smith, Sammamish, WA (US)

(73) Assignee: Physio-Control, Inc., Redmond, WA (US)

( * ) Notice: Subject to any disclaimer, the term of this patent is extended or adjusted under 35 U.S.C. 154(b) by 190 days.

(21) Appl. No.: 16/548,641

(22) Filed: Aug. 22, 2019

(65) Prior Publication Data
US 2019/0381307 A1    Dec. 19, 2019

Related U.S. Application Data

(63) Continuation of application No. 14/827,271, filed on Aug. 15, 2015, now Pat. No. 10,391,296.

(60) Provisional application No. 62/042,190, filed on Aug. 26, 2014.

(51) Int. Cl.
*A61N 1/00* (2006.01)
*A61N 1/02* (2006.01)
*G08B 21/18* (2006.01)
*G16H 40/40* (2018.01)
*A61N 1/39* (2006.01)

(52) U.S. Cl.
CPC .......... *A61N 1/025* (2013.01); *A61N 1/3904* (2017.08); *G08B 21/18* (2013.01); *G16H 40/40* (2018.01); *A61N 1/3993* (2013.01)

(58) Field of Classification Search
CPC .... A61N 1/025; A61N 1/3904; A61N 1/3993; G08B 21/18; G16H 40/40
See application file for complete search history.

(56) References Cited

U.S. PATENT DOCUMENTS

| 8,844,803 | B2 | 9/2014 | Otech et al. | |
|---|---|---|---|---|
| 2006/0259080 | A1 | 11/2006 | Vaisnys et al. | |
| 2008/0136652 | A1 | 6/2008 | Vaisnys et al. | |
| 2013/0087609 | A1* | 4/2013 | Nichol | G06F 16/23 235/375 |
| 2014/0296755 | A1* | 10/2014 | Lack | A61G 7/0514 601/149 |
| 2015/0169916 | A1* | 6/2015 | Hill | G01S 5/0268 340/10.1 |
| 2015/0265844 | A1* | 9/2015 | Powers | A61N 1/3943 607/6 |

(Continued)

OTHER PUBLICATIONS

Office Action for U.S. Appl. No. 14/827,271, dated Nov. 3, 2017, Hoss, "Matrix-Coded AED Maintenance," 9 pages.

(Continued)

*Primary Examiner* — Scott M. Getzow
(74) *Attorney, Agent, or Firm* — Lee & Hayes, P.C.

(57) ABSTRACT

A status monitoring function that simplifies the process of collecting status information for medical devices in a medical device system. Matrix codes are used to associate a medical device with a location. A maintenance application transmits the association information to a centralized tracking system. Status information about the medical device is also transmitted to the centralized tracking system from the maintenance application.

20 Claims, 8 Drawing Sheets

(56) References Cited

U.S. PATENT DOCUMENTS

2016/0125765 A1    5/2016   Meretei et al.

OTHER PUBLICATIONS

Office Action for U.S. Appl. No. 14/827,271, dated Feb. 6, 2019, Hoss, "Matrix-Coded AED Maintenance," 6 pages.
Office Action for U.S. Appl. No. 14/827,271, dated Mar. 20, 2017, Hoss, "Matrix-Coded AED Maintenance," 8 pages.
Office Action for U.S. Appl. No. 14/827,271, dated Jul. 6, 2016, Hoss, "Matrix-Coded AED Maintenance," 5 pages.
Office Action for U.S. Appl. No. 14/827,271, dated Aug. 31, 2018, Hoss, "Matrix-Coded AED Maintenance," 9 pages.

* cited by examiner

DEFIBRILLATION SCENE

| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |

TWO MAIN TYPES OF EXTERNAL DEFIBRILLATORS

Fig. 3   COMPONENTS OF EXTERNAL DEFIBRILLATOR

Initialization

Maintenance

MATRIX-CODED MEDICAL DEVICE TRACKER AND MAINTENANCE

CROSS REFERENCE TO RELATED APPLICATIONS

This patent application is a continuation of U.S. application Ser. No. 14/827,271, filed Aug. 15, 2015, which will issue on Aug. 27, 2019 as U.S. Pat. No. 10,391,296, which claims the benefit of and priority to U.S. Provisional Patent Application Ser. No. 62/042,190, filed on Aug. 26, 2014, entitled "QR Code AED Maintenance," the disclosures of which are hereby incorporated by reference for all purposes.

TECHNICAL FIELD

The disclosed subject matter pertains generally to the area of medical devices, and more specifically to the area of wireless medical device maintenance.

BACKGROUND INFORMATION

Health care providers often deploy medical device systems to facilitate the provision of health care services. In particular, emergency medical health care providers may employ a number of individual devices, such as external defibrillators, for use in providing health care services. Because of the nature of the service, maintaining the medical device system in operable condition is extremely important. Accordingly, monitoring the operability status of each medical device in the medical device system is very important.

Known in the art are systems that enable an organization to monitor status information about medical devices in a medical device system. Certain improvements have enabled advanced medical devices to report certain fundamental status information to a central monitoring facility. However, for the most part, such organizations require individuals to manually inspect and record the readiness status for many if not all the medical devices in the medical device system. The individuals must then enter that readiness status into a portal, and use that portal to track all the medical devices. However, such a system is labor intensive and prone to human error.

A superior status monitoring ability for use in a medical device system has eluded those skilled in the art, until now.

SUMMARY OF EMBODIMENTS

Embodiments are directed to a status monitoring function that simplifies the process of collecting status information for medical devices in a medical device system. In one embodiment, a medical device system is provided that includes a plurality of medical devices, each medical device having an associated location at which the medical device is intended to reside, the medical device having a first matrix code encoded with status information about the medical device, the associated location having a second matrix code encoded with location information, the medical device and the associated location being co-located; a tracking system configured to maintain information about an operability status of the medical device system; and a maintenance application configured to scan the first matrix code and the second matrix code, to decode the information encoded within the first matrix code and the second matrix code, and to transmit the information to the tracking system.

In another embodiment, a method of maintaining a medical device is provided that includes associating a location matrix code with a location; generating a status matrix code for the medical device, the status matrix code uniquely identifying the medical device; associating the location matrix code with the medical device; and storing the association of the location matrix code with an identification of the medical device in a status data store.

DETAILED DESCRIPTION

Generally described, the disclosure is directed to a medical device system that employs matrix codes to encode information about medical devices in the system, including status and location data. The information is scanned by a mobile device and transmitted to a central location. Specific embodiments and implementations are described below.

Description of Operative Environment for Embodiments

Figures 1, 2:
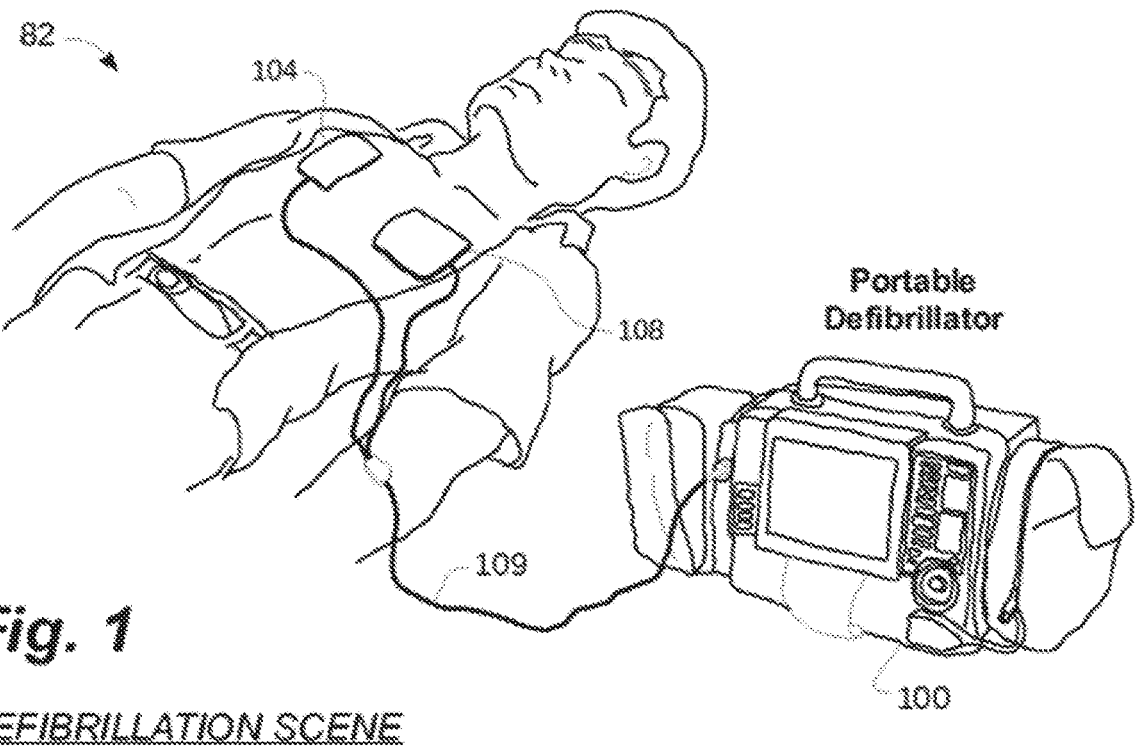
FIG. 1 is a diagram of a scene where an external defibrillator is used to try and save the life of a person in accordance with an embodiment.
FIG. 2 is a table listing two main types of the external defibrillator shown in FIG. 1, and by whom they might be used.

FIG. 1 is a diagram of a defibrillation scene. A person 82 is lying supine. Person 82 could be a patient in a hospital or someone found unconscious. Person 82 is experiencing a medical emergency, which could be, by way of an example, Ventricular Fibrillation (VF).

A portable external defibrillator 100 has been brought close to person 82. The portable external defibrillator can also be a hybrid monitor/defibrillator 82. At least two defibrillation electrodes 104, 108 are usually provided with external defibrillator 100. Electrodes 104, 108 are coupled with external defibrillator 100 via electrode leads 109. A rescuer (not shown) has attached electrodes 104, 108 to the skin of person 82. Defibrillator 100 is monitoring cardiac rhythms and potentially administering, via electrodes 104, 108, a brief, strong electric pulse through the body of person 82. The pulse, also known as a defibrillation shock, goes through the person's heart in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing examples of types of external defibrillators and their primary intended users. A first type of defibrillator 100 is generally called a defibrillator-monitor (or monitor-defibrillator) because it is typically formed as a single unit in combination with a patient monitor. Alternatively, the defibrillator-monitor may be a modular device with separable components. For example, in one alternative embodiment, the defibrillator-monitor may include a base component and a plurality of detachable pods. Each pod communicates with the base component, perhaps wirelessly. Certain pods may be used to collect information about a patient, such as vital statistics. One example of such an alternative system is described in U.S. Pat. No. 8,738,128 entitled "Defibrillator/Monitor System Having A Pod With Leads Capable Of Wirelessly Communicating," the disclosure of which is hereby incorporated by reference for all purposes. A defibrillator-monitor is intended to be used by medical professionals, such as doctors, nurses, paramedics, emergency medical technicians, etc. Such a defibrillator-monitor is generally intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals, such as a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator." An AED typically makes the shock/no shock determination by itself, automatically. It can typically sense enough physiological conditions of the person 82 using only the defibrillation electrodes 104, 108 shown in FIG. 1. An AED can either administer the shock automatically, or instruct the user to do so, e.g. by pushing a button.

There are other types of external defibrillators in addition to those listed in FIG. 2. For example, a hybrid defibrillator can have aspects of an AED and also of a defibrillator-monitor. A usual such aspect is additional ECG monitoring capability.

Figure 3:
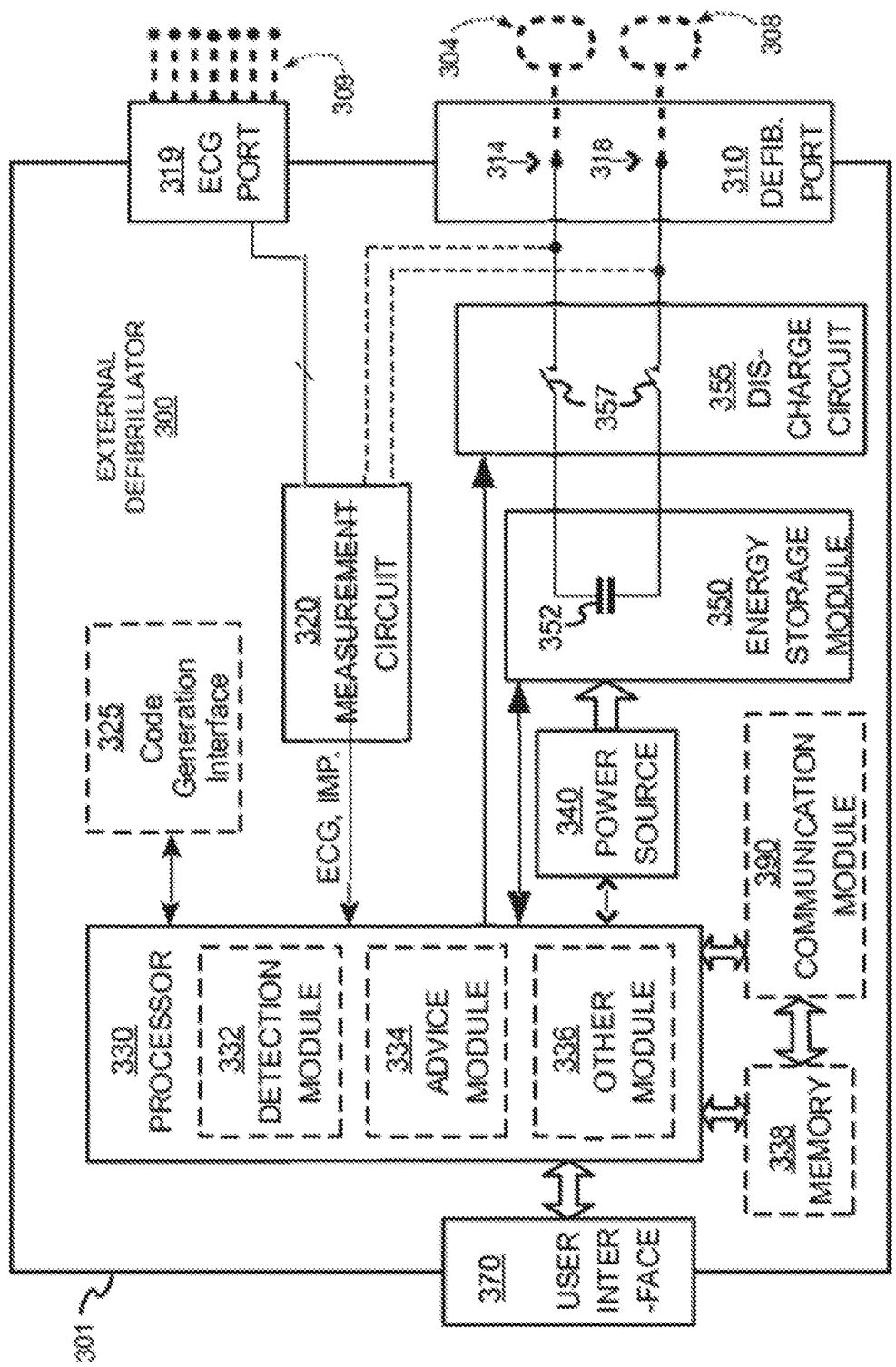
FIG. 3 is a diagram showing components of an external defibrillator made according to embodiments.

FIG. 3 is a diagram showing components of an external defibrillator 300 made according to embodiments. These components can be, for example, in external defibrillator 100 of FIG. 1. Plus, the components shown in FIG. 3 can be provided in a housing 301, also known as a casing.

External defibrillator 300 is intended for use by a user, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding an electrical charge to person 82 via electrodes 304, 308. The electrical charge may be stored in defibrillator 300, as discussed below.

If defibrillator 300 is a defibrillator-monitor, as was described with reference to FIG. 2, it will frequently also have an ECG port 319 in housing 301, for plugging in ECG lead wires 309. ECG lead wires 309 can sense an ECG signal, such as any of the ECG lead signals that comprise a common 12-lead ECG recording. Other types of ECG lead signals are equally applicable. A defibrillator-monitor could have additional ports that are not shown.

In one embodiment, the defibrillator 300 may include a code generation component 325. In one specific implementation, the code generation component 325 includes functions and operations to interact with processor 330 (described below) to test and evaluate the status of operation of various other components of the defibrillator 300. The code generation component 325 is also configured to dynamically generate a matrix code (described below) that includes information derived from or summarizing the results of the tests and evaluations of the other components. The code generation component 325 may additionally include unique identifying information about the defibrillator 300, such as a model number and/or serial number, into the matrix code.

Defibrillator 300 also includes a measurement circuit 320. Measurement circuit 320 receives physiological signals from ECG port 319, and also from other ports, if provided. These physiological signals are sensed, and information about them is rendered by measurement circuit 320 as data, or other signals, etc.

Defibrillator 300 also includes a processor 330, which may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions too numerous to list here. In addition, if flow monitor component 325 is provided, it may be implemented as a module executing, at least in part, within processor 330.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. In addition, memory 338 can store prompts for the user, etc. Moreover, memory 338 can store patient data, such as, for example, data regarding how much fluid may have been administered to patient 82 as detected by the flow monitor component 325.

Defibrillator 300 may also include a power source 340. To enable portability of defibrillator 300, power source 340 typically includes a battery. Such a battery is typically implemented as a battery pack, which can be rechargeable or not. Sometimes, a combination of rechargeable and non-rechargeable battery packs is used. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, or the like.

Defibrillator 300 moreover includes a discharge circuit 355. Discharge circuit 355 can be controlled to permit the energy stored in module 350 to be discharged to nodes 314, 318, and thus also to defibrillation electrodes 304, 308. Discharge circuit 355 can include one or more switches 357. Those can be made in a number of ways, such as by an H-bridge, or the like.

Defibrillator 300 further includes a user interface 370. User interface 370 can be made in any number of ways. For example, interface 370 may include a screen, to display what is detected and measured, provide visual feedback to a rescuer for their resuscitation attempts, and so on. User interface 370 may also include a speaker to issue audible signals, such as voice prompts, or the like. The user interface 370 may issue prompts to the user, visually or audibly, so that the user can administer CPR, for example. Interface 370 may additionally include various controls, such as pushbuttons, keyboards, touch screens, and so on. In addition, discharge circuit 355 can be controlled by processor 330, or directly by user via user interface 370, and so on. The user interface 370 may also be used to display a matrix code generated by the code generating component XXX.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

Embodiments of a Coded Maintenance System of Medical Devices

Figure 4:
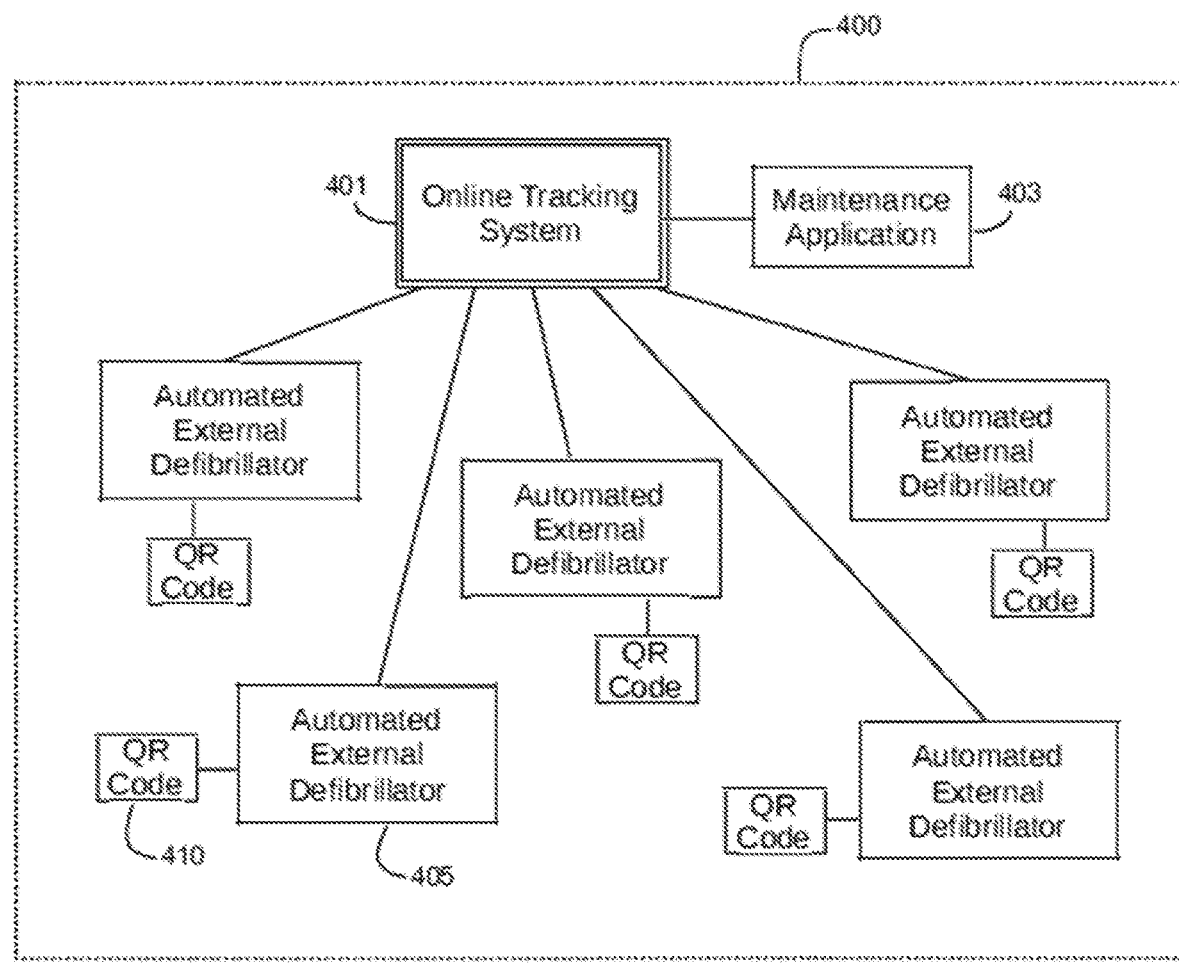
FIG. 4 is a functional block diagram generally illustrating a medical device system in accordance with one embodiment.

Turning first to FIG. 4, embodiments are disclosed that provide a medical device system 400 for use in providing medical care to patients experiencing a medical event away from a hospital. In one embodiment, the medical device system 400 includes a group of medical devices, such as Automated External Defibrillator (AED) 405, an online tracking system 401, and a maintenance application 403. The online tracking system 401 may be a component of an electronic patient care reporting system used to deliver immediate, vital information about patients undergoing medical care away from a hospital. Generally stated, the medical device system 400 is deployed by a health care provider and enables the aggregation and immediate reporting of patient data from the field to a health care treatment facility, such as a hospital. For example, if AED 405 is used to provide urgent medical care to a patient experiencing sudden cardiac arrest in the field (e.g., away from a hospital), information about the care being provided is transmitted to the online tracking system 401 for relay to a health care treatment facility, such as a hospital or urgent care facility. Providing patient care information in this manner provides the treatment facility with crucial information earlier than it would otherwise have the information and improving the care that can be delivered to the patient once the patient arrives at the treatment facility. One example of such a patient care reporting system is the LIFENET system developed by Physio-Control, Inc. of Redmond, Wash.

Typically, the medical device system 400 includes a plurality of medical devices, such as AEDs or the like. To simplify discussion, the medical devices will be referred to herein as AEDs, although it should be appreciated that any form of medical device may be used in the medical device system 400, not only AEDs or not even only defibrillators. For example, many medical devices may equally benefit from the disclosed embodiments, such as first aid kits, epinephrine auto-injectors, or any other medical device for which its status and/or location constitute important information. Accordingly, the term "medical devices" should be read to include any such products. To enhance and ensure the operation of the medical device system 400 generally, the online tracking system 401 maintains status and location information (among other information) for each of the AEDs in the system 400, such as AED 405. In this embodiment, a maintenance application 403 is used to provide and update the status and location information for each of the AEDs to the online tracking system 401.

The maintenance application 403 may take many forms, and may be implemented as a Web-based application accessible over a wide-area network, such as the Internet, or as a function on a mobile device, such as a hand-held cellular telephone or tablet. Preferably, the maintenance application 403 is implemented as an application executable on a mobile computing device, such as a "smartphone," a tablet computing device, or portable computer. The maintenance application 403 enables a user to input various information about the several medical devices in the medical device system 400. For instance, the maintenance application 403 may be used to input or update status information about the AED 405. Examples of the type of status information that may be reported includes whether the AED 405 is operable and charged, whether its electrodes have exceeded their useful life, whether the AED 405 has passed any self-test operations it may perform. Other indicators may include: Ready or Not Ready; battery low or expired; electrodes not connected or expired; some other device issue; no communication signal or a low communication signal; failed self-test operations; physical damage to the device; or the like. Also, a "Help" section may be provided which enters a help request for that specific device.

In addition to the operational status of the AED 405, the online tracking system 401 should be made aware of the location of the AED 405. In other words, for the entire mobile device system 400 to be considered fully operational, each of the medical devices within it (e.g., AED 400) should not only be operational but also resident at the proper pre-designated location.

Figure 5:
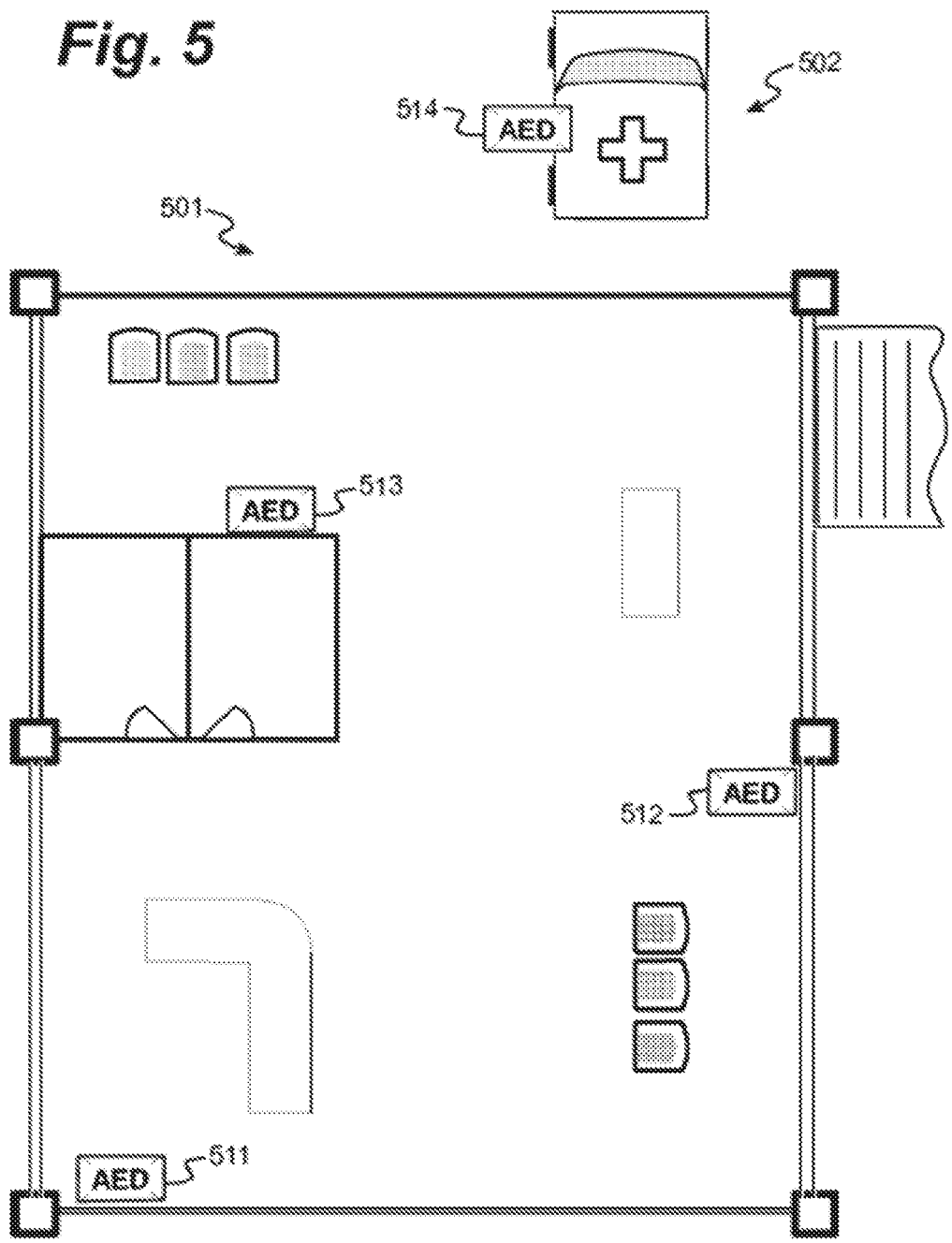
FIG. 5 is a conceptual floor plan (not to scale) of an example facility in which are distributed a number of medical devices at strategic locations.

To illustrate the point, and referring briefly to FIG. 5, the medical device system 400 may be implemented as a group of AEDs distributed at strategic locations throughout a facility, such as an airport, office complex, shopping mall, or any other facility. Shown in FIG. 5 is a conceptual floor plan (not to scale) of an example facility 501 in which are distributed three AEDs (AED1 511, AED2 512, and AED3 513). In accordance with some operational guidance, each of the AEDs is deployed at generally strategic locations within the facility 501 so as to reduce or minimize the distance from a medical emergency and any particular AED. Accordingly, the location of each AED within the facility 501 is important information that should be identified to the online tracking system 401.

The medical device system 400 may also include medical devices that are more mobile in nature. For instance, the medical device system 400 may include an ambulance 502, which is by its nature not fixed to a specific geographic location. However, a specific medical device (e.g., AED4 514) should be associated with the ambulance 502 such that the online tracking system 401 can be made aware of whether AED4 514 is in fact resident on the ambulance 502 wherever it may be.

Returning to FIG. 4, this embodiment makes use of matrix codes (e.g., QR Code 410) to convey the desired status and location information for each of the mobile devices in the mobile device system 400. Generally stated, matrix codes are two-dimensional barcodes, which are machine-readable optical labels that are encoded with information about the item to which it is attached. Typically, a matrix code is comprised of black modules (square dots) arranged in a square grid on a white background, which can be read by an imaging device (such as a camera, scanner, etc.) and are processed using error correction until the image can be appropriately interpreted. The embedded data are then extracted from patterns that are present in both horizontal and vertical components of the matrix code. Perhaps the most common form of matrix code is referred to as a "Quick Response Code" or just QR Code.

Figure 6:
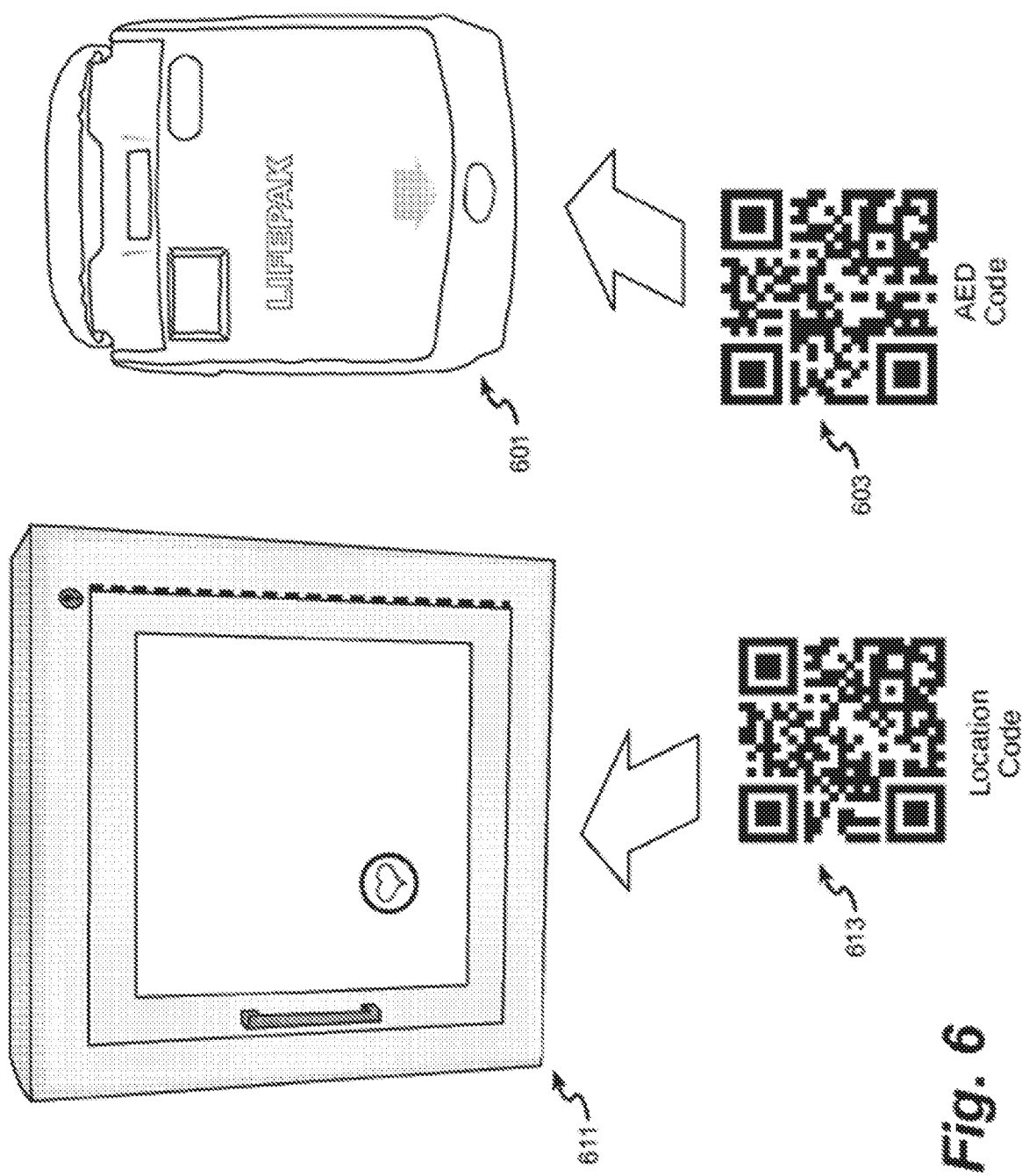
FIG. 6 is a diagram generally illustrating a medical device (e.g., an AED) and a location (e.g., a cabinet) at which the medical device may be stored.

Turning now to FIG. 6, an embodiment is explained with reference to an illustration of an example AED 601 and an AED cabinet 611. In this embodiment, the AED 601 represents one of any number of medical devices that are deployed in a medical device system, such as the system described above. The cabinet 611 represents one of any number of locations at which a medical device should reside. Although illustrated as a conventional cabinet that may be mounted on a wall, the cabinet 611 is illustrative only and merely represents a location, which may be either fixed (e.g. a wall cabinet) or mobile (e.g., an ambulance). In addition, and as explained in greater detail below, the cabinet 611 may include integrated optical scanning and reporting capability as an alternative to a separate portable scanning component.

In this embodiment, a first matrix code (AED Code 603) has been created and is affixed to the AED 601. As will be apparent, a matrix code can be encoded with a substantial amount of information. In one example, the AED code 603 may be encoded with the model number of the AED 601, the serial number of the particular AED 601 to which the matrix code is affixed, and various other data about the particular AED 601. Similarly, a second matrix code (location code 613) is affixed to a particular location at which a medical device should be resident. Referring briefly to FIG. 5, the locations shown on the floor plan of the facility 501 would correspond to a location, as well as the ambulance 502.

The matrix codes may be affixed to their respective objects (e.g., AED 601 or cabinet 611) in any acceptable manner. For example, the matrix codes may be printed on stickers and affixed to the object. Alternatively, one or both of the matrix codes could be printed directly on the object, such as during production or using mobile printing equipment.

Figure 7:
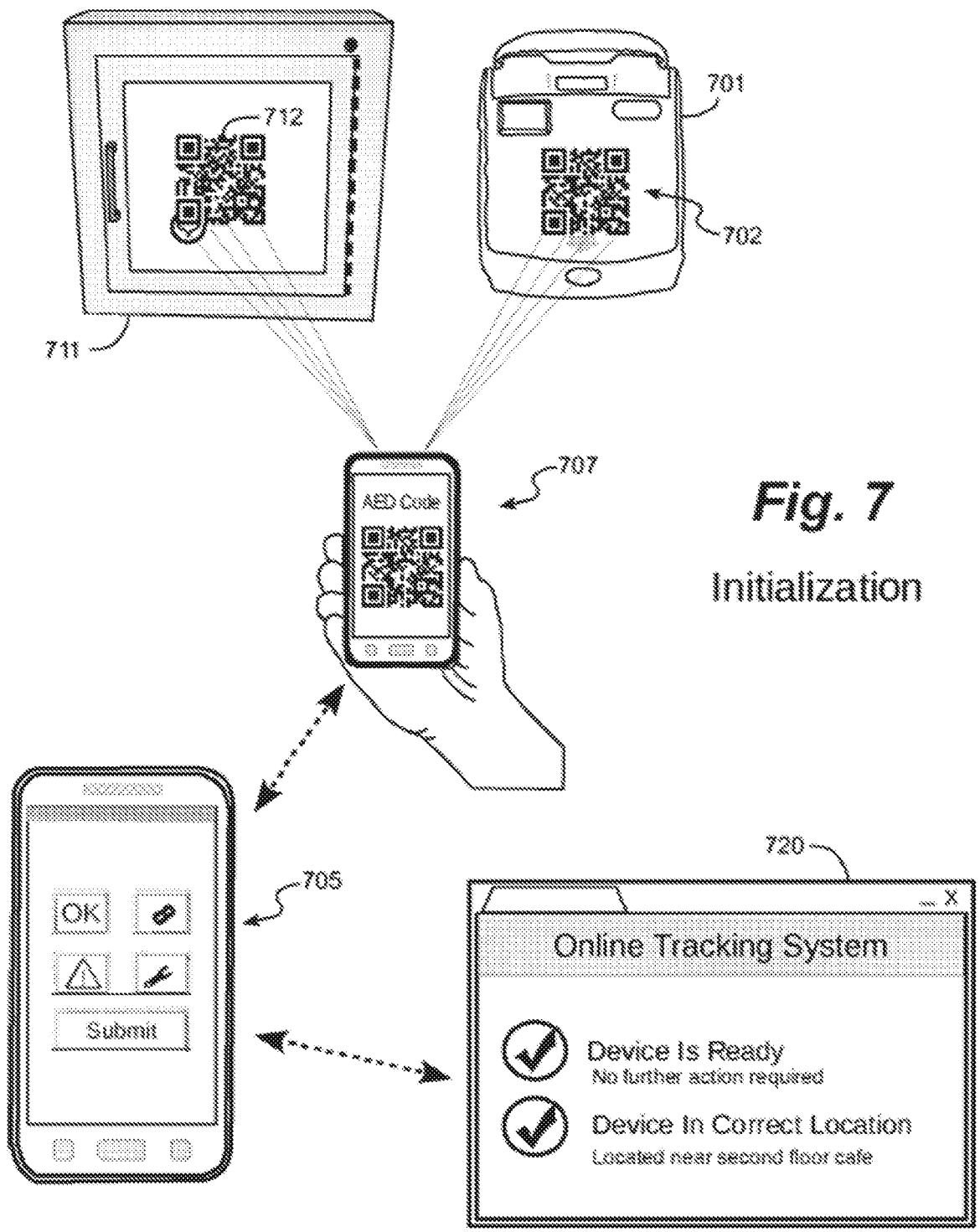
FIG. 7 is a conceptual illustration of an initialization procedure that may be used to register a new medical device, such as an AED, with a medical device system.

FIG. 7 is a conceptual illustration of an initialization procedure that may be used to register a new medical device, such as AED 701, with a medical device system. In this embodiment, each medical device, such as AED 701, is affixed with a unique AED matrix code 702 and every location 711 is affixed with a unique location matrix code 712. To register the AED 701 with the system, a subscriber employs a maintenance application installed on a mobile device 707, such as a cellular telephone or tablet, to scan the matrix codes. The maintenance application enables the subscriber to associate the AED matrix code 702 to the location matrix code 712. The subscriber may then upload the association information to the online tracking system 720. In this way, the online tracking system 720 maintains information that identifies where each medical device is stored and the status of each medical device. The use of mobile devices, such as cellular telephones or tablet computing devices, enables wireless and immediate update of the status of each medical device.

In one implementation, the subscriber creates the association between the medical device and the location by scanning the matrix codes for the several devices and locations during an initialization phase. For example, a subscriber may physically visit each location at which a medical device is intended and scan the location matrix code 712 at that location 711. The particular location associated with each location matrix code may be preassigned. For instance, as part of an initial design of the medical device system, a geographic layout may be created during which particular geographic and/or functional locations (e.g., an ambulance) may be identified and a location matrix code created for each one pre-encoded with the appropriate location data. Alternatively, the subscriber may remotely create location matrix codes at the time of deployment. For instance, the maintenance application may include a matrix code generation element that can encode the current location (e.g., derived from GPS or other location information provided by the host mobile device) and remotely print the matrix code for attachment to the location (e.g., an AED cabinet). In yet another alternative, the location matrix code may be pre-encoded with a unique identifier, and when the location matrix code is affixed to the location, the current location is then derived from GPS or other location detection component of the host mobile device. That current location information may then be associated with the unique identifier for that location matrix code.

The subscriber also scans the AED matrix code 702 for the medical device resident at that location 711. In one enhancement, the subscriber also examines the operational status of the medical device and uploads that data to the online tracking system. The maintenance application provides a simple interface 705 to allow the subscriber to provide device readiness options, which may include, for example: Ready/Not Ready, Battery Low/Expired, Electrodes Disconnected, Electrodes Expired, Device Failed a Self-Test, other Device Issue, No Communication Signal, Poor Communication Signal, or any other operational status information. The information verified may resemble similar information that medical devices with remote connectivity functionality (e.g, WiFi or cellular connectivity) may provide automatically. The subscriber may also be presented with a Help option to enable the subscriber to submit a help request for that specific device.

In another embodiment, the maintenance application and scanning device may be implemented directly in the location 711, such as within a smart cabinet or carrying bag. In this embodiment, the location includes an optical viewing function and, possibly, communication functions. Using those integrated functions, the location may directly scan or observe the AED 701 and/or the AED matrix code 702. In such an alternative embodiment, the location matrix code 707 may be eliminated in lieu of a location 705 that is designated and encoded with its own location information.

Once the appropriate data are scanned and/or provided to the maintenance application, the maintenance application may automatically, or in response to some user action like pressing a submit button, transmit the data (status data and location data) to the online tracking system 720 for entry into a readiness profile for that particular AED 701. The maintenance application may also include a timestamp and/or an indicator of the subscriber currently using the maintenance application, such as the subscriber's login ID or the like.

Subscribers may then access the data using the online tracking system 750 either directly from the maintenance application, or alternatively using a common computing system, such as over the Internet or, perhaps, using a virtual private network. Accessing the online tracking system 720, the subscriber can review and confirm the readiness status of each individual medical device and, concomitantly, the entire medical device system. Errors or alerts may be raised by the online tracking system 720, such as by transmitting an electronic message to an administrator or the like.

Figure 8:
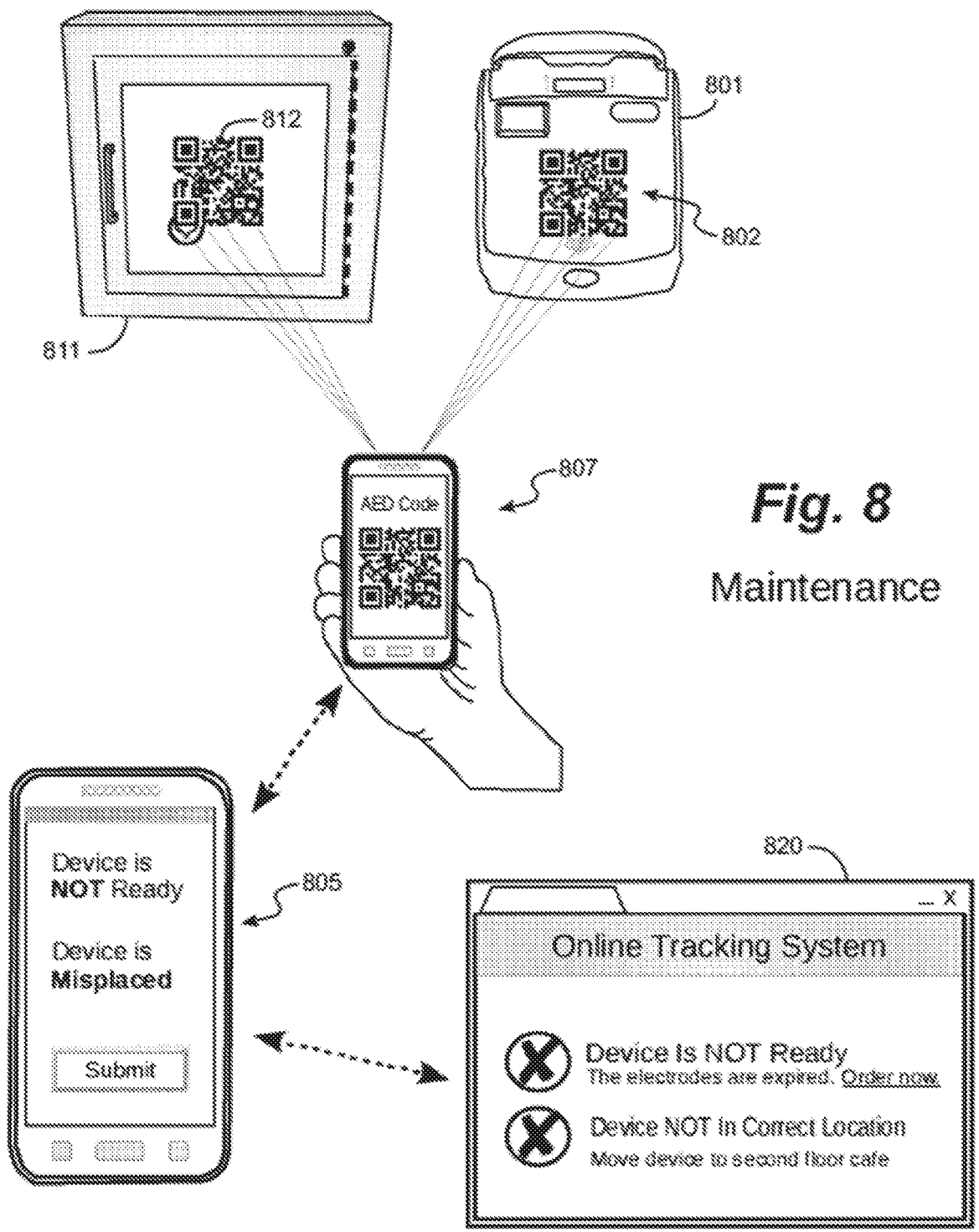
FIG. 8 is a conceptual illustration of an example maintenance inspection of medical devices that may be conducted by a subscriber in accordance with one embodiment.

FIG. 8 is a conceptual illustration of an example maintenance inspection that may be conducted by a subscriber using one embodiment. In this example, a subscriber is performing an inspection of one or more medical devices that have been deployed in a medical device system such as described above. The subscriber visits each location at which a medical device has been deployed. At the location, the subscriber uses a maintenance application 805 resident on a mobile device (e.g., a smartphone, tablet computer, special-purpose mobile scanner, or the like) to scan the location matrix code 812 affixed to the location 811, and the AED matrix code 802 associated with the AED 801. The maintenance application may be the same application discussed above, or it may be a similar application used for maintenance tasks.

Once the AED matrix code 802 and the location matrix code 812 have been scanned using a mobile device 807, the maintenance application 805 transmits the data to the online tracking system 820. The online tracking system 820 evaluates the data to determine the status of the AED 801 as well as whether the AED 801 is in the correct location. For example, if the data transmitted by the maintenance application 805 reveals that the AED 801 is in the wrong location, the online tracking system 820 may issue an error to that effect. The online tracking system 820 may notify the subscriber that the AED 801 is in the wrong location, where the AED 801 should be located, and which other AED 801 should be in that location 811. Similarly, any problems with the operational status of the AED 801 may be reported to the online tracking system 820.

As discussed above, the maintenance application 805 may allow the subscriber to manually enter any status information about the AED 801 derived from an inspection of the AED 801. Such information may be detected by the subscriber querying the AED 801 for such information, perhaps using a control panel on the AED 801. In an alternative embodiment, the AED 801 includes a display that shows a dynamically-generated matrix code that is encoded with status information about the AED 801. As is known in the art, matrix codes may be easily generated with any desired information. Accordingly, in this embodiment, the AED 801 may perform any one or more of many self-tests to identify any operational issues it may have. A unique matrix code may be dynamically generated upon request that reflects the results of those self-tests. In addition, the display used to show the dynamically-generated matrix code may be implemented using extremely low power technology, such as an interferometric modulator display or an electrophoretic ink display, for example. In that way, should the AED 801 be non-functional because of a discharged or damaged battery, the matrix code may still be visible. In this embodiment, when the subscriber scans the AED matrix code 802, the readiness information is automatically detected because it is encoded within the AED matrix code 802.

Once the data has been uploaded to the online tracking system 820, it stores that data for use by the medical device system. Should any problems be detected, the online tracking system 820 may return additional information to assist the subscriber to remedy any problems if possible. For example, if the problem identified is that electrodes attached to the AED 801 are expired, the online tracking system 820 may provide information to enable the subscriber to order new electrodes, such as a phone number for customer service and a direct link to a webstore at which the subscriber may acquire new electrodes. This is but one example, and many other types of information are possible. Other readiness indicators may also have an explanatory section with information about what the subscriber could or should do next.

In yet another enhancement, if the AED matrix code 802 is dynamically generated, it could also be generated with an overlaid logo or text to indicate the status of the AED 801. For example, if no problems are detected, an "OK" may be displayed on the AED matrix code 802. If problems are detected, an indicator to that effect (e.g., a large "X" or the like) could be displayed on the AED matrix code 802. It will be appreciated that matrix codes typically employ sufficient error correction that such a logo or text may be used without harming the information encoded within the matrix code.

In still another embodiment, the maintenance application and scanning device may be implemented directly in the location, such as within a smart cabinet or carrying bag. In this embodiment, the location includes an optical viewing function and, possibly, communication functions. Using those integrated functions, the location may directly scan or observe the AED 801 and/or the AED matrix code 802.

Figure 9:
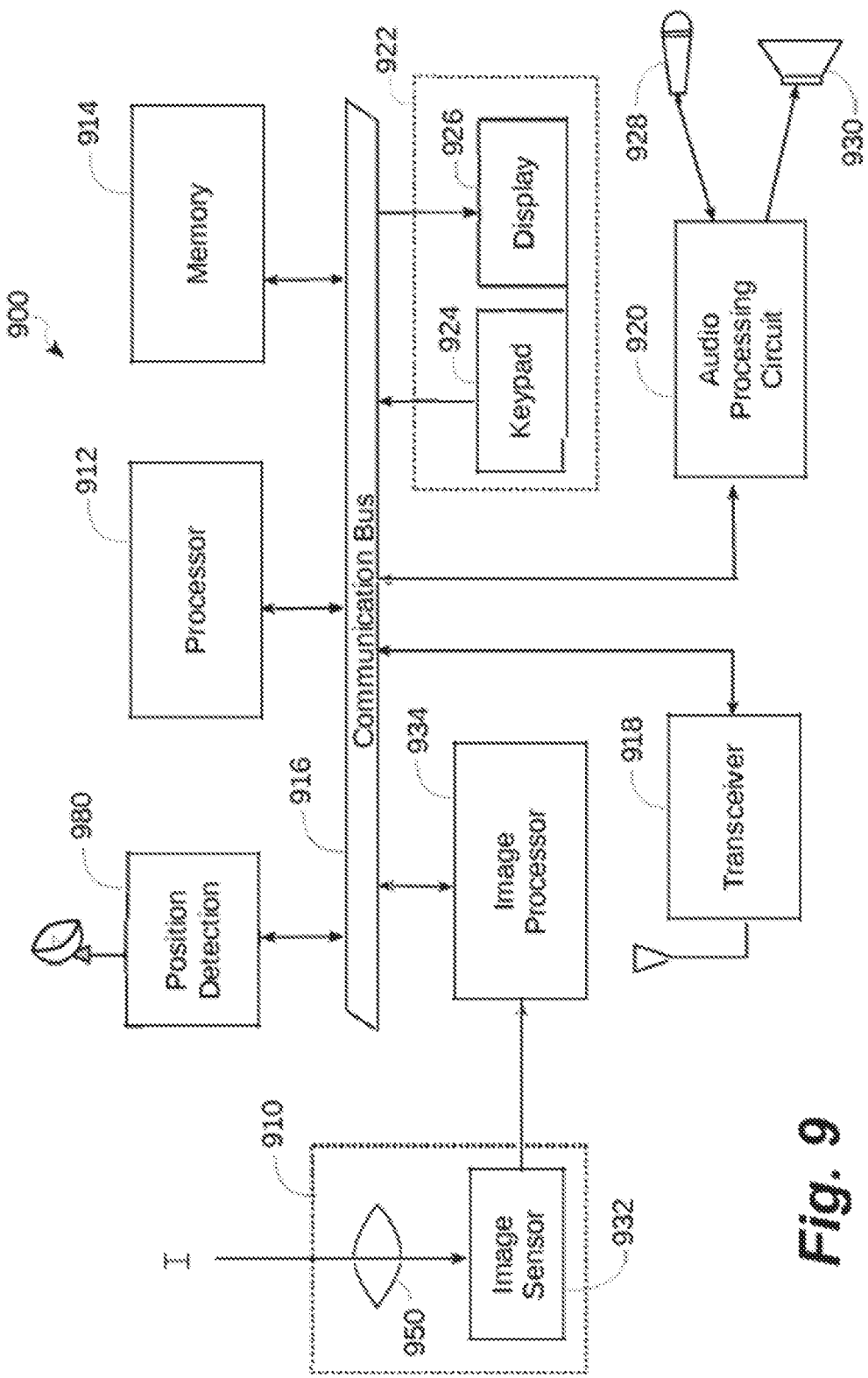
FIG. 9 is a functional block diagram generally illustrating one possible example of a mobile device that may be used in various embodiments.

FIG. 9 is a functional block diagram generally illustrating one possible example of a mobile device 900 that may be used in various embodiments. As shown, mobile device 900 includes several functional components to enable scanning matrix codes and transmitting information. The example mobile device may be implemented as one or more of any number of portable devices, such as a mobile phone, a tablet computer, a personal digital assistant, a notebook or ultrabook computer, or the like. Alternatively, the mobile device could be implemented as a component in a location-aware cabinet or other housing for a portable medical device. For example, the example mobile device could be implemented as an AED containment bag including a camera and electronics, or as a cabinet in which an AED or other medical device should be stored.

The mobile device 900 comprises a processor 912, a memory 914, communication circuit 916, transceiver 918, audio processing circuit 920, user interface 922, image sensor 932, image processor 934, and optical system 950. Microprocessor 912 controls the operation of the mobile device 900 according to programs stored in program memory 914. The communication circuit 916 interfaces the microprocessor 912 with the various other components, such as the user interface 922, transceiver 918, audio processing circuit 920, and image processing circuit 934. User interface 922 may include a keypad 924 and a display 926. Keypad 924 allows the operator to key in alphanumeric characters, enter commands, and select options. The display 926 allows the operator to view output data, such as entered information, output of the mobile device 900, images or other media, and other service information. In certain mobile devices, the user interface 922 combines the keypad 924 and the display 926 into a touchpad display.

The mobile device 900 also includes a microphone 928 and speaker 930 though certain mobile communication devices, such as a PDA or palm-top computer may not have such features. Microphone 928 converts sounds into electrical audio signals, and speaker 930 converts audio signals into audible sound. Audio processing circuit 920 provides basic analog output signals to the speaker 930 and accepts analog audio inputs from the microphone 928. Transceiver 918 is coupled to an antenna 936 for receiving and transmitting signals on a suitable communications network (not shown).

Image sensor 932 captures images formed by light impacting on the surface of the image sensor 932. The image sensor 932 may be any conventional image sensor 932, such as a charge-coupled device (CCD) or complementary metal oxide semiconductor (CMOS) image sensor. Additionally, the image sensor 932 may be embodied in the form of a modular camera assembly with or without an integrated optical system 950. Image processor 934 processes raw image data collected by the image sensor 932 for subsequent output to the display 926, storage in memory 914, or for transmission by the transceiver 918. The image processor 934 is a conventional signal microprocessor programmed to process image data, which is well known in the art. A position sensor 980 detects the position of the mobile device 900 and generates a position signal that is input to the microprocessor 912. The position sensor 980 may be a Global Positioning System sensor, potentiometer, or other measuring device known in the art of electronics.

Other embodiments may include combinations and subcombinations of features described or shown in FIGS. 3-9, including for example, embodiments that are equivalent to providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, "feature" or "features" can refer to structures and/or functions of an apparatus, article of manufacture or system, and/or the steps, acts, or modalities of a method.

In the foregoing description, numerous details have been set forth in order to provide a sufficient understanding of the described embodiments. In other instances, well-known features have been omitted or simplified to not unnecessarily obscure the description.

A person skilled in the art in view of this description will be able to practice the disclosed invention. The specific embodiments disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

What is claimed is:

1. A system, comprising:
   a medical device configured to output a matrix code and a nonencoded indicator overlaying the matrix code, the matrix code indicating an identifier of the medical device or a proper position of the medical device; and
   a scanning device comprising:
      an imaging sensor configured to capture an image depicting the matrix code and the nonencoded indicator output by the medical device;
      a position sensor configured to identify a position of the scanning device;
      a processor;
      memory storing instructions that, when executed by the processor, cause the processor to perform operations comprising:
         generating a first signal comprising data representing the image and the position of the scanning device; and
         outputting a notification in response to a second signal, the notification indicating that the medical device is in an improper location; and
      a transceiver configured to transmit the first signal to an external system and to receive the second signal from the external system.

2. The system of claim 1, wherein the scanning device further comprises:
   a display,
   wherein outputting the notification based on the second signal comprises causing the display to output a visual indication that the medical device is in the improper location.

3. The system of claim 1, wherein the nonencoded indicator comprises text, a symbol, a letter, a word, or a picture, and
   wherein the medical device comprises a defibrillator, a first aid kit, or an epinephrine auto-injector.

4. The system of claim 1, wherein the medical device comprises:
   a processor configured to perform a self-test of the medical device; and
   a display configured to output the matrix code and the nonencoded indicator, and
   wherein the matrix code indicates a result of the self-test, and
   wherein the nonencoded indicator indicates the result of the self-test.

5. The system of claim 4, wherein the medical device further comprises:
a battery;
a detection circuit;
a defibrillation circuit;
an electrode; and
a communication circuit, and
wherein the processor is configured to perform the self-test of the medical device by:
determining whether a charge level of the battery is below a threshold charge level;
determining whether the electrode is expired;
determining whether the electrode is connected to the detection circuit or the defibrillation circuit; or
determining whether the communication circuit has received a communication signal.

6. A method performed by a scanning device, the method comprising:
identifying an image of a code displayed on a medical device, the image depicting a nonencoded indicator overlaying the code, the nonencoded indicator comprising a letter, a word, or a picture;
determining a proper location of the medical device by processing the image;
determining a location of the medical device or of the scanning device;
determining that the location of the medical device is different than the proper location of the medical device; and
outputting an instruction to relocate the medical device.

7. The method of claim 6, wherein the medical device comprises a defibrillator, a first aid kit, or an epinephrine auto-injector.

8. The method of claim 6, wherein the scanning device comprises a mobile computing device.

9. The method of claim 6, wherein the code comprises a matrix code displayed by the medical device.

10. The method of claim 6, wherein determining the proper location of the medical device by processing the image comprises:
generating a first signal comprising data representing the image;
transmitting the first signal to an external device; and
receiving a second signal from the external device, the second signal comprising data representing the proper location of the medical device.

11. The method of claim 10, wherein transmitting the first signal to the external device comprises wirelessly transmitting the first signal, and
wherein receiving the second signal from the external device comprises wirelessly receiving the second signal.

12. The method of claim 6, further comprising:
determining an operational status of the medical device; and
outputting a notification indicating the operational status of the medical device.

13. The method of claim 12, wherein the operational status of the medical device comprises an operational status of a battery.

14. The method of claim 12, wherein the operational status of the medical device comprises an operational status of a defibrillator electrode.

15. A computing device, comprising:
an imaging sensor configured to capture an image depicting a code and a nonencoded indicator displayed by a medical device, the nonencoded indicator overlaying the code and comprising a letter, a word, or a picture;
a processor; and
memory storing instructions that, when executed by the processor, cause the processor to perform operations comprising:
determining a proper location of the medical device by processing the image;
determining a location of the medical device or of the computing device;
determining that the location of the medical device is not the proper location of the medical device; and
outputting an instruction to relocate the medical device.

16. The computing device of claim 15, wherein the medical device comprises a defibrillator, a first aid kit, or an epinephrine auto-injector.

17. The computing device of claim 15, wherein the code comprises a matrix code displayed by the medical device.

18. The computing device of claim 15, further comprising:
a transceiver configured to transmit a first signal to an external device and to receive a second signal from the external device,
wherein determining the proper location of the medical device by processing the image comprises:
generating the first signal to comprise data representing the image;
determining the proper location of the medical device by analyzing the second signal.

19. The computing device of claim 15, wherein the operations further comprise:
determining an operational status of the medical device; and
outputting a notification indicating the operational status of the medical device.

20. The computing device of claim 15, wherein determining the proper location of the medical device by processing the image comprises determining the proper location of the medical device encoded by the code.

* * * * *